(12) United States Patent
Åhnblad et al.

(10) Patent No.: US 12,251,531 B2
(45) Date of Patent: Mar. 18, 2025

(54) PLUG FOR INSERTION INTO THE NOSE OR EAR OF A SUBJECT AND METHOD FOR ADMINISTERING A FLUID THERAPEUTIC AGENT USING SAID PLUG

(71) Applicant: Hogne AB, Nacka (SE)

(72) Inventors: Susanne Åhnblad, Stockholm (SE); Peter Åhnblad, Muskö (SE)

(73) Assignee: HOGNE AB, Nacka (SE)

( * ) Notice: Subject to any disclaimer, the term of this patent is extended or adjusted under 35 U.S.C. 154(b) by 1028 days.

(21) Appl. No.: 17/095,844

(22) Filed: Nov. 12, 2020

(65) Prior Publication Data

US 2021/0069481 A1 Mar. 11, 2021

Related U.S. Application Data

(63) Continuation-in-part of application No. 17/062,589, filed on Oct. 4, 2020, which is a continuation of
(Continued)

(30) Foreign Application Priority Data

May 13, 2019 (SE) .................................... 1950566-8

(51) Int. Cl.
*A61M 31/00* (2006.01)
*A61F 11/08* (2006.01)
(Continued)

(52) U.S. Cl.
CPC ............. *A61M 31/00* (2013.01); *A61F 11/08* (2013.01); *A61M 5/30* (2013.01); *A61F 11/085* (2022.01); *A61M 2205/3317* (2013.01); *A61M 2205/3327* (2013.01); *A61M 2205/3375* (2013.01); *A61M 2205/75* (2013.01); *A61M 2210/0618* (2013.01);
(Continued)

(58) Field of Classification Search
CPC .................... A61M 31/00; A61M 5/30; A61M 2205/3317; A61M 2205/3327; A61M 2205/3375; A61M 2205/75; A61M 2210/0618; A61M 2210/0662; A61F 11/08; A61F 11/085; G10K 11/1752; H04R 1/1016; H04R 25/652
See application file for complete search history.

(56) References Cited

U.S. PATENT DOCUMENTS

2006/0253087 A1* 11/2006 Vlodaver ............ A61M 3/0287
604/212
2013/0310805 A1 11/2013 Yadidi
(Continued)

FOREIGN PATENT DOCUMENTS

KR 200482070 Y1 * 12/2016 ............. A61H 35/04

*Primary Examiner* — Rebecca E Eisenberg
*Assistant Examiner* — Rachel O'Connell
(74) *Attorney, Agent, or Firm* — Ballard Spahr LLP

(57) ABSTRACT

A plug for insertion into the nose or ear of a subject, comprising: a body adapted to fit into a nostril or ear canal of the subject and a hollow tubular member with a collar disposed inside the body. The plug is adapted to receive a tip of a syringe for injection of a fluid therapeutic agent through the hollow tubular member for nasal administration or administration to the ear. A kit comprising the plug and a syringe, as well as a method for administering a fluid therapeutic agent to a subject using the plug are also disclosed.

17 Claims, 6 Drawing Sheets

Related U.S. Application Data application No. PCT/SE2020/050491, filed on May 13, 2020.

(51) Int. Cl.
| | | |
|---|---|---|
| *A61M 5/30* | (2006.01) | |
| *G10K 11/175* | (2006.01) | |
| *H04R 1/10* | (2006.01) | |
| *H04R 25/00* | (2006.01) | |

(52) U.S. Cl.
CPC . *A61M 2210/0662* (2013.01); *G10K 11/1752* (2020.05); *H04R 1/1016* (2013.01); *H04R 25/652* (2013.01)

(56) References Cited

U.S. PATENT DOCUMENTS

| | | | |
|---|---|---|---|
| 2016/0361203 A1* | 12/2016 | Khademhosseini | A61M 1/85 |
| 2017/0014272 A1* | 1/2017 | Ray | A61F 11/00 |
| 2019/0230450 A1* | 7/2019 | Aase | H04R 25/405 |
| 2019/0253793 A1* | 8/2019 | Pedersen | H04R 25/60 |
| 2021/0060233 A1* | 3/2021 | Kim | A61M 3/0262 |

\* cited by examiner

PLUG FOR INSERTION INTO THE NOSE OR EAR OF A SUBJECT AND METHOD FOR ADMINISTERING A FLUID THERAPEUTIC AGENT USING SAID PLUG

CROSS-REFERENCE TO RELATED APPLICATIONS

This application is a continuation-in-part of U.S. non-provisional application Ser. No. 17/062,589, titled "Nasal Plug" and filed on Oct. 4, 2020, which is a continuation of International Application No. PCT/SE2020/050491, filed May 13, 2020, which claims the benefit of Swedish Patent Application No. SE 1950566-8, filed May 13, 2019. The entire contents of all of the above-mentioned applications are hereby incorporated by reference.

TECHNICAL FIELD

The present solution relates to a plug for insertion into the nose or ear, more precisely a nostril or ear canal, of a subject. The plug may be used to administer fluid therapeutic agents to the subject, specifically for, but not limited to, treatment of conditions affecting the nose or ear.

BACKGROUND ART

The human nose is a delicate organ not only for the olfaction, the sense of smell, but also for heating, filtration, and humidification of the inhaled air. The nasal sinuses will also "boost" the inhaled air with nitrogen oxide (NO), a gaseous signaling molecule that increases the pulmonary blood flow and oxygen uptake. The total surface area available in this richly vascularized respiratory mucosa is estimated to be about 180 $cm^2$.

Nasal mucosal capillaries are specifically designed for rapid passage of fluids through the vascular wall and out into the dry air in the nose. The amount of blood flow to this area is considerable—it is higher per unit of tissue than the blood flow to the brain, liver or muscle.

The nose-brain pathway across the olfactory mucosa transports nasally delivered medication directly into the cerebrospinal fluid (CSF) and brain—leading to early effects of centrally acting medications. Other conventionally delivery methods such as intravenous or intramuscular must deal with the blood-brain barrier.

The nasal mucosa easily absorbs medications directly into the venous circulation. Because the absorptive surface is not the intestinal mucosa, as for oral or rectal medications, the drug never enters the liver circulation and is not subjected to hepatic (liver) metabolism—thereby leading to far higher drug absorption and efficacy. Hence, nasal administration of medical substances provides several advantages over injection using hypodermic needles.

One way of nasal administration is by using nasal sprays. However, the amount of substance which may be administered is limited due to discomfort when too much liquid is introduced into the nasal cavity and the difficulty in retaining the substance in the nasal cavity.

It is also well-known in the art to provide nose plugs which are coated or soaked with for instance hemostatic compounds to promote blood clotting and stop nosebleed. WO 2018/076118 A1 and WO 2010/085196 A1 disclose examples of such nose plugs. However, the amount of substance which may be administered by such soaked or coated plugs is similarly limited by the volume or surface of the plug, and absorption is essentially limited to the part of the nasal mucosa in contact with the plug. Thus, there is a need for improved devices and methods for nasal drug administration which overcome the disadvantages of the prior art.

SUMMARY OF INVENTION

It is an object of the solution to address at least some of the problems and issues outlined above. It is possible to achieve these objects and others by providing a plug according to the present disclosure.

The above plug may be configured and implemented according to different optional embodiments. Further possible features and benefits of this solution will become apparent from the detailed description below.

In a first aspect of the present disclosure, there is provided a plug for insertion into the nose or ear of a subject, comprising: a body adapted to fit into a nostril or ear canal of the subject, the body comprising a first end arranged to face inward and a second end arranged to face outward during use; a hollow tubular member disposed inside the body and comprising a first opening facing inwardly and a second opening facing outward during use, the hollow tubular member being arranged to provide fluid communication between the first and second openings; wherein the tubular member further comprises a collar disposed inside the body; and wherein the second opening of the hollow tubular member is adapted to receive a tip of a syringe for injection of a fluid therapeutic agent through the hollow tubular member.

In one embodiment, the plug further comprises a spray nozzle arranged adjacent the first opening of the hollow tubular member. The spray nozzle facilitates efficient distribution of the fluid therapeutic agent into the nasal cavity or ear.

In one embodiment, the plug further comprises a filter arranged inside the hollow tubular member. The filter protects the nose or ear from inhaled, intruding, infiltrated or penetrating particles such as dust, dirt, smoke, pollen, carcinogens, radioactive substances, and other irritants, and/or microbes such as bacteria, parasites, amoebae, fungi, viruses (e.g. causing flu, common cold, and other airborne pandemic respiratory diseases, MERS, SARS-CoV, SARS-CoV-2 etc).

In one embodiment, the plug further comprises an internal device arranged inside the hollow tubular member. The internal device can be controlled via an app and can, for example, be used as an alarm clock or in virtual reality situations and emit designated scents/fragrances, vibrations, acoustic signals etc. as feedback or to notify the wearer of different situations that might arise and require his/her attention or action.

In one embodiment, the internal device is an acoustic device being selected from a hearing aid, a speaker or an auditory masking device. The acoustic device provides the possibility to combine the plug with a wide range of technical applications such as audio communication, listening to music, detect auditory vibrations, acoustic trauma or inhibiting tinnitus by producing sound or noise.

In one embodiment, the internal device is a sensor, the sensor being configured to detect gas (suffocating e.g. nitrogen, carbon dioxide, argon, flammable e.g. gasoline, hydrogen, methane, propane, toxic e.g. hydrogen sulfide, carbon monoxide, nitric oxide) detect radioactivity, detect levels of pollen, pollution or pathogens, acoustic signals and/or electromagnetic signals.

In one embodiment, the sensor is configured to emit pheromones, aphrodisiac, scents/fragrances, vibrations and/ or acoustic signals in response to the detection of any of the substances described above. This may be used to alert the wearer of hazard or danger and prompt the user to take suitable action.

Many agents cannot be smelled by humans and that can be life threatening in different environments, and with a small sensor in the nose plug one can immediate get notifications (by emitting different stimuli) about it. Also, many people suffer from more or less total loss of smell (anosmia) and a sensor placed in the plug has the advantage of being very close to the olfactory area (area for receptors for smell) up in the nose, and can enhance the smell and increase the quality of life.

In one embodiment, the internal device is configured to determine a position and/or orientation of the plug. Examples of suitable internal devices include positioning or tracking devices such as markers or beacons emitting and/or receiving electromagnetic signals which may be used to determine the position, gyroscopes, accelerometers etc.

In a second aspect of the present disclosure, there is provided a kit comprising at least one plug for insertion into the nose or ear of a subject and at least one syringe pre-filled with a fluid to be injected into the nostril or ear canal of the subject through the plug, the plug comprising: a body adapted to fit into a nostril or ear canal of the subject, the body comprising a first end arranged to face inward and a second end arranged to face outward during use; a hollow tubular member disposed inside the body and comprising a first opening facing inwardly and a second opening facing outward during use, the hollow tubular member being arranged to provide fluid communication between the first and second openings; wherein the tubular member further comprises a collar disposed inside the body; and wherein the second opening of the hollow tubular member is adapted to receive a tip of the syringe for injection of a fluid therapeutic agent through the hollow tubular member.

In one embodiment, the plug further comprises a spray nozzle arranged adjacent the first opening of the hollow tubular member.

In one embodiment, the plug further comprises a filter arranged inside the hollow tubular member.

In one embodiment, the plug further comprises an internal device arranged inside the hollow tubular member. The internal device can be controlled via an app and can, for example, be used as an alarm clock or in virtual reality situations and emit designated scents/fragrances, vibrations, acoustic signals etc. as feedback or to notify the wearer of different situations that might arise and require his/her attention or action.

In one embodiment, the internal device is an acoustic device being selected from a hearing aid, a speaker or an auditory masking device. The acoustic device provides the possibility to combine the plug with a wide range of technical applications such as audio communication, listening to music, detect auditory vibrations, acoustic trauma or inhibiting tinnitus by producing sound or noise.

In one embodiment, the internal device is a sensor, the sensor being configured to detect gas (suffocating e.g. nitrogen, carbon dioxide, argon, flammable e.g. gasoline, hydrogen, methane, propane, toxic e.g. hydrogen sulfide, carbon monoxide, nitric oxide) detect radioactivity, detect levels of pollen, pollution or pathogens, acoustic signals and/or electromagnetic signals.

In one embodiment, the sensor is configured to emit pheromones, aphrodisiac, scents/fragrances, vibrations and/or acoustic signals in response to the detection of any of the substances described above. This may be used to alert the wearer of hazard or danger and prompt the user to take suitable action.

Many agents cannot be smelled by humans and that can be life threatening in different environments, and with a small sensor in the nose plug one can immediate get notifications (by emitting different stimuli) about it. Also, many people suffer from more or less total loss of smell (anosmia) and a sensor placed in the plug has the advantage of being very close to the olfactory area (area for receptors for smell) up in the nose, and can enhance the smell and increase the quality of life.

In one embodiment, the internal device is configured to determine a position and/or orientation of the plug. Examples of suitable internal devices include positioning or tracking devices such as markers or beacons emitting and/or receiving electromagnetic signals which may be used to determine the position, gyroscopes, accelerometers etc.

In one embodiment, the fluid therapeutic agent is selected from analgesics, corticosteroids, antibiotics, decongestants, stem cells, nicotine, vaccines, cerebral cytostatic, disinfectants, astringents, procoagulants, antifungals, cerumenolytics.

In a third aspect of the present disclosure, there is provided a method for administering a fluid therapeutic agent to a subject, comprising: providing a plug for insertion into the nose or ear of a subject, the plug comprising: a body adapted to fit into a nostril or ear canal of the subject, the body comprising a first end arranged to face inward and a second end arranged to face outward during use; a hollow tubular member disposed inside the body and comprising a first opening facing inwardly and a second opening facing outward during use, the hollow tubular member being arranged to provide fluid communication between the first and second openings; wherein the tubular member further comprises a collar disposed inside the body, and wherein the second opening of the hollow tubular member is arranged to receive the tip of a syringe for injection of a fluid through the hollow tubular member, inserting the plug into a nostril or ear canal of the subject; fitting a syringe filled with a fluid therapeutic agent to the second opening of the hollow tubular member; and injecting the fluid therapeutic agent through the hollow tubular member into the nose or ear of the subject.

By injecting the fluid therapeutic agent into the nose or ear through the plug, administration of both topical and systemic substances is facilitated whilst the plug seals the nostril or ear canal such that the fluid therapeutic agent remains within the nasal cavity or ear for long-lasting action and/or absorption.

In one embodiment, the plug is provided with a spray nozzle arranged adjacent the first opening of the hollow tubular member such that injecting causes distribution of the fluid therapeutic agent over an area of the nostril or ear canal of the subject.

In one embodiment, the plug is used to treat a condition affecting the nose or ear of the subject, the condition being selected from nosebleed (epistaxis), swimmer's ear (otitis externa), earwax (cerumen impaction) and/or fungal infection (otomycosis).

In one embodiment, the plug is used for nasal systemic drug delivery or olfactory transfer of the fluid therapeutic agent. The nasal mucosa provides a large surface area for absorption of systemically acting substances. Intranasal delivery provides a practical, non-invasive method of bypassing the blood-brain barrier to deliver therapeutic agents to the brain and spinal cord. The plug allows drugs that do not cross this barrier to be delivered to the central nervous system within minutes.

In one embodiment, the fluid therapeutic agent is selected from analgesics, corticosteroids, antibiotics, decongestants, stem cells, nicotine, vaccines, cerebral cytostatic, disinfectants, astringents, procoagulants, antifungals, and/or cerumenolytics.

The aspects and embodiments described herein are freely combinable with each other.

BRIEF DESCRIPTION OF DRAWINGS

The solution will now be described, by way of example, with reference to the accompanying drawings, in which.

DESCRIPTION OF EMBODIMENTS

In the following, a detailed description of the different embodiments of the solution is disclosed with reference to the accompanying drawings. All examples herein should be seen as part of the general description and are therefore possible to combine in any way in general terms. Individual features of the various embodiments may be combined or exchanged unless such combination or exchange is clearly contradictory to the overall function of the implementation.

Briefly described, the present disclosure relates to a plug 1 arranged to be inserted into the nostril 2 or ear canal 3 of a subject, to serve as a delivery pathway for administration of fluid therapeutic agents, in addition to e.g. stopping a nosebleed. In the context of the present disclosure, the terms 'distal' and 'proximal' when referring to the plug 1 and its components should be interpreted from the point of view of a person handling the plug 1, regardless whether the subject and the person handling the plug 1 is the same or different persons.

Figure 1A:
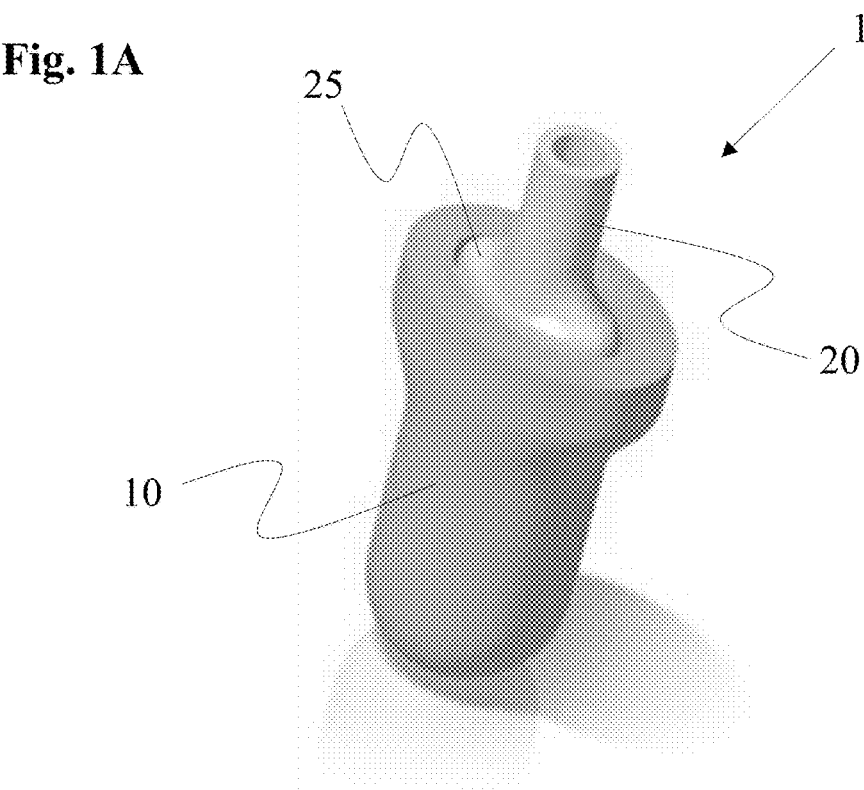
FIG. 1A is a perspective view of a plug with a tubular member and a collar according to one embodiment of the present disclosure.
Figure 1B:
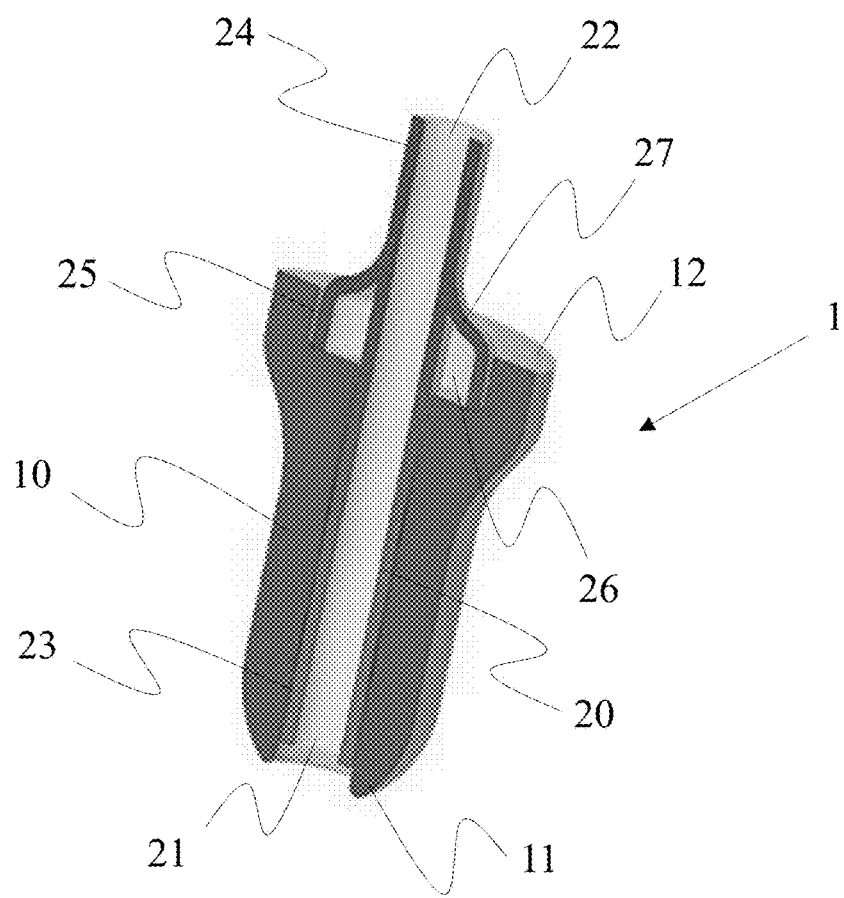
FIG. 1B is a cross-sectional view of a plug with a tubular member and a collar according to one embodiment of the present disclosure.

In FIGS. 1a and 1b, perspective and cross-sectional views, respectively, of a plug 1 according to the present disclosure. The plug 1 comprises a body 10 and a hollow tubular member 20 disposed inside the body 10. The body 10 comprises a first end 11 and a second end 12 which substantially coincide or correspond with first and second ends 21, 22, respectively, of the hollow tubular member 20 when inserted.

The hollow tubular member 20 comprises a substantially cylindrical tube with a first opening 21 in a first end 23 and a second opening 22 in a second end 24 thereof. Additionally, the tubular member 20 comprises a collar 25 arranged on the external surface and extending outward. In one embodiment, the collar 25 is shaped like a cup, with a substantially concave side 26 facing towards the first end 23 and a substantially convex side 27 facing towards the second end 24. In one embodiment, the collar 25 is oval or elliptic, wherein the width is given by the minor and major axes of the ellipse, respectively. I.e. the widest transverse extension of the collar 25 corresponds to the major axis of the ellipse, corresponding to the sectional plane shown in FIG. 1B. In one embodiment, the tubular member 20 comprises a flexible material, e.g. a thermoplastic material which is flexible yet provides a certain stiffness.

The first end 11 of the body 10 is arranged to face inwardly when inserted into the nostril 2 or ear canal 3 of the subject during use. Conversely, the second end 12 is arranged to face outward during use. As such the first opening 21 of the tubular member 20 faces inwardly and the second opening 22 faces outward during use of the plug 1.

The plug 1 according to the present disclosure provides an effective treatment of nosebleed in that the absorbent body 10 applies direct pressure to the site of the nosebleed due to the resilient properties of the body 10 and absorbs the blood exiting the wound site. In cases of excessive and/or prolonged bleeding, the collar 25 forms a stop which effectively prevents blood from escaping the body 10 and thus avoids dripping from a saturated plug 1. Additionally, the collar 25 acts like an umbrella to push the body 10 outward to stabilize and aid in applying pressure on the walls of the nostril 2.

At the same time, the tubular member 20 provides a fluid passage for air which enables the subject to continue breathing through the nose 5 even with the plug 1 inserted in the nostril 2.

In one embodiment, the body 10 comprises a compressible, resilient foam material adapted to absorb liquid, i.e. blood from the subject. Examples of suitable materials for the body 10 include polyurethane (PU) foam, polyether foam, (poly) ethylene-vinyl acetate (EVA/PEVA) foam, foam materials from forestry and agricultural byproducts based on organic cellulose or hemi-cellulose and special woven cotton, so called cotton-foam. In one embodiment, the foam material exhibits micropores.

Figure 6:
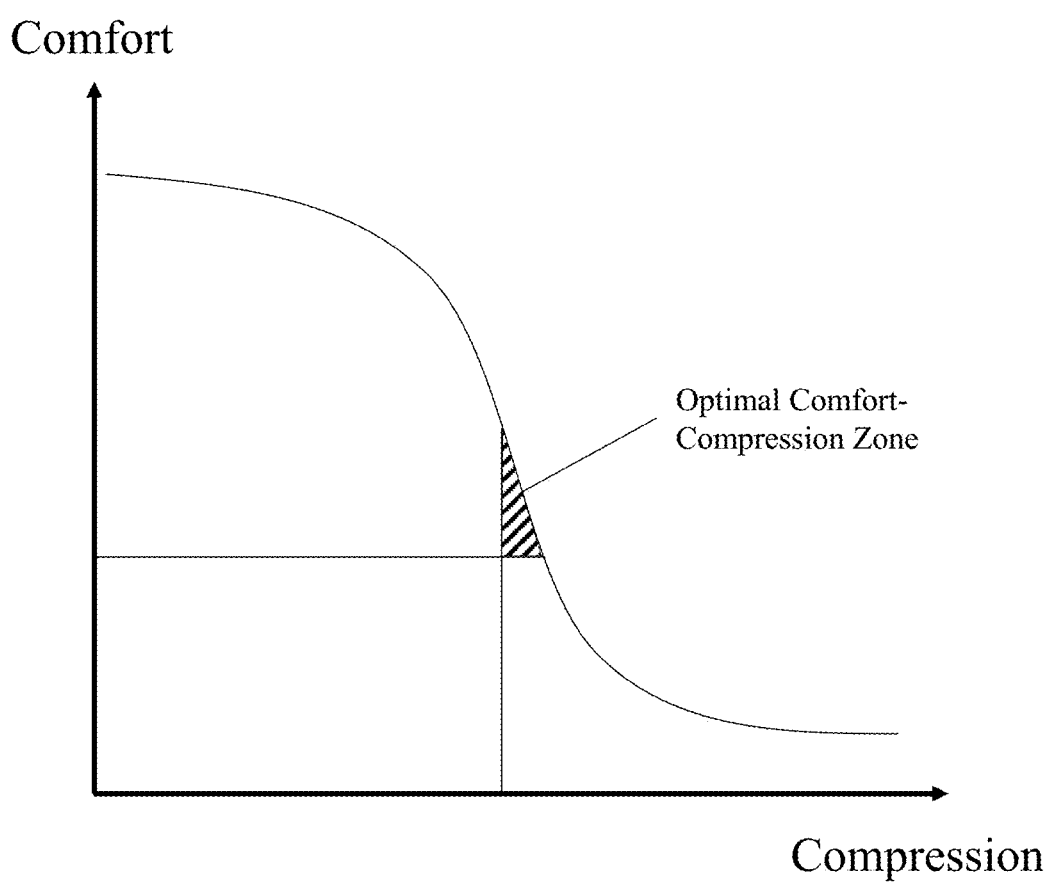
FIG. 6 is a diagram illustrating the relationship the relationship between the comfort experienced by a subject and the compression of the plug according to one embodiment of the present disclosure when inserted into the nostril or the ear canal of the subject.

With reference to FIG. 6, there is shown a diagram illustrating the relationship between the comfort experienced by a subject using the plug 1 and the compression of the plug 1 when inserted into the nostril 2 or the ear canal 3, i.e. a measure of how much pressure the plug 1 exerts on the surrounding walls of the nostril 2 or ear canal 3. The compression is therefore related to the resilience and compressibility of the foam material of the body 10 of the plug 1. On the left-hand side of the graph, the user experiences a high level of comfort whereas the compression is relatively low. As the compression of the plug 1 increases, i.e. a higher pressure is exerted by the plug 1, the comfort level decreases, eventually reaching a low level of comfort when the compression is high on the right-hand side of the graph.

In order to achieve the purposes of the present disclosure with respect to the sealing effect to prevent injected fluid substances from escaping the nose or ear, it is vital to have sufficient compression of the plug 1. However, if the pressure exerted by the plug 1 is too high, the user is less likely to accept prolonged use of the plug 1 which is necessary for some treatments as will be further explained below. Therefore, with the aim to optimize the compression/pressure exerted by the plug 1 in relation to the comfort experienced by the user, an optimal comfort-compression zone has been identified as illustrated by the triangular shaped area marked by diagonal lines in FIG. 6. The optimal comfort-compression zone is delimited by a horizontal line at approximately one third of the comfort level experienced with no to little compression, a vertical line at approximately half the maximum compression, and the graph representing the relationship between the comfort and compression. It is understood that the comfort level can vary between individuals, which may give rise to slight modifications to location of the optimal comfort-compression zone.

In one embodiment, the body 10 is coated or soaked with a hemostatic agent to promote blood clotting and stop bleeding. Examples of suitable hemostatic agents include calcium alginate naturally present in e.g. brown algae (i.e. seaweed extracts), glycine, calcium, kaolin, zeolite, topical microfibrillar collagen, micro-dispersed oxidized cellulose and chitosan derived from shells of shrimp and other sea crustaceans. Other suitable substances include hyaluronic acid for regeneration and botulinum toxin for runny nose (vasomotor rhinitis).

In one embodiment, the body 10 is coated or soaked with an aroma compound to be inhaled by the subject. Examples of suitable aroma compounds include menthol, peppermint, lubricating oils such as sesame oil, saline gels, Aloe vera or liquid paraffin which lubricate the mucosa in the nostril to prevent dehydration and formation of cracks or fissures and reduce the risk of rebleeding.

Figure 2A:
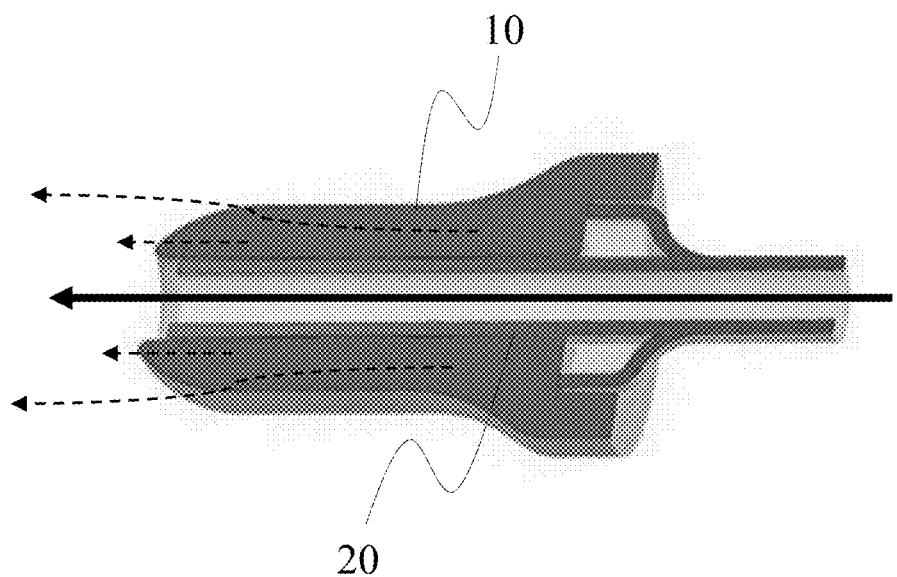
FIGS. 2A and 2B are cross-sectional views of a plug soaked with a substance according to one embodiment of the present disclosure illustrating inhaling and exhaling, respectively.

Referring now to FIG. 2A, when the subject inhales through the plug 1, the air passes through the tubular member 20, illustrated by the solid arrow. As a result, near the first opening 21 a local vacuum is formed which acts to draw the substance out from the body 10 of the plug 1 such that it is mixed with the inhaled air, illustrated by the dashed arrows. With every breath, a small amount of the substance from the soaked micropore foam plug 1 is drawn out and added to the inhaled air for prolonged action.

Figure 2B:
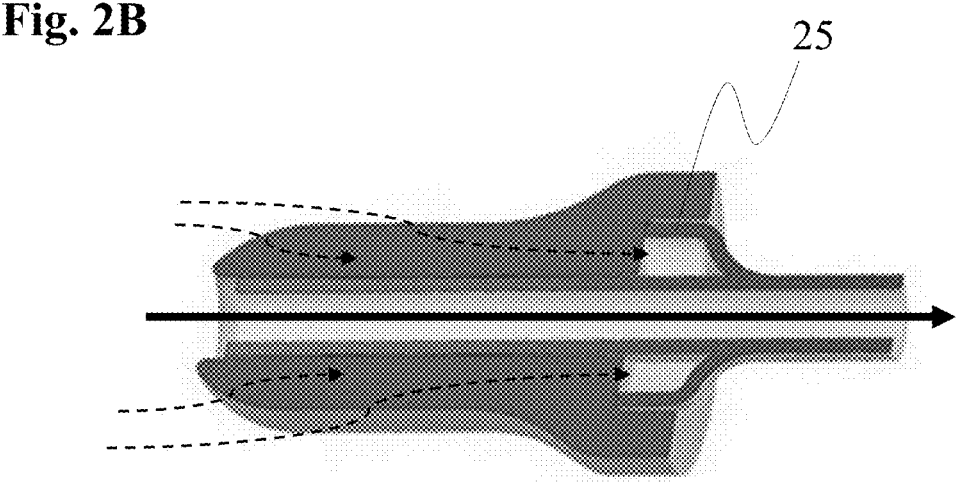

Referring now to FIG. 2B, when the subject exhales through the plug 1, the air again passes through the first opening of the tubular member 20, illustrated by the solid arrow. Conversely to inhalation, due to the reduced diameter of the tubular member 20 compared to the nostril, the pressure in the nostril proximal to the plug 1 increases. A small part of the exhaled air together with the substance will enter the body 10 of the plug 1, illustrated by the dashed arrows, but the collar 25 acts to retain the substance in the body 10. Thus, the collar 25 prevents the substance to be inhaled by the subject from exiting the plug 1, but instead retaining the substance in the body 10. This substance-saving feature reduces the amount of substance required for the treatment.

The plug 1 and/or body 10 may in one embodiment have an oval-shaped transverse cross-section, wherein the width of the plug 1 is greater in the transverse extension corresponding to the major axis of the collar 25 as shown in FIG. 1B. In one embodiment, the plug 1 and/or body 10 is bell-shaped with a substantially cylindrical central portion, wherein the first end 11 is substantially hemispherical or dome-shaped and the second end 12 is flared outward. In one embodiment, the width of the collar 25 corresponding to the major axis of the oval shape is substantially equal to or greater than the width of the body 10. Thus, the collar 25 when inserted will stretch and push the body 10 outward. Thus, the plug 1 exerts a pressure on the nostril 2 or ear canal 3 to create a seal.

When used to stop nosebleed, the plug 1 will brace against the lateral wall of the nostril 2 to increase the pressure against the bleed site, e.g. Kiesselbach's plexus. At the same time, the subject can breathe through the hollow tubular member 20. In one embodiment, the total dry weight of the plug is less than 1 gram. The absorbing capacity is about 2.5 milliliters of blood, plus expandable extra 0.5-1.0 milliliters which is estimated to be more than enough for absorbing the blood leakage during an average anterior nose bleeding The tubular member 20 and the body 10 have substantially equal length, although in one embodiment the tubular member 20 is slightly offset from the body 10 such that the first end 23 of the tubular member 20 is arranged proximal to the first end 11 of the body 10, and the first opening 21 is sunk into the body 10. In this way, the first (distal) end 23 of the tubular member 20 is shielded inside the body 10 of the plug 1 during insertion, to reduce the risk of damaging the nasal mucosa or epithelium of the ear canal 3. In one embodiment, the tubular member 20 protrudes from the second end 12 of the body 10, i.e. the second (proximal) end 24 of the tubular member 20 extends further proximally than the body 10 to provide a grip when handling the plug 1 during insertion into and removal from the nostril 2 or ear canal 3.

Figure 3:
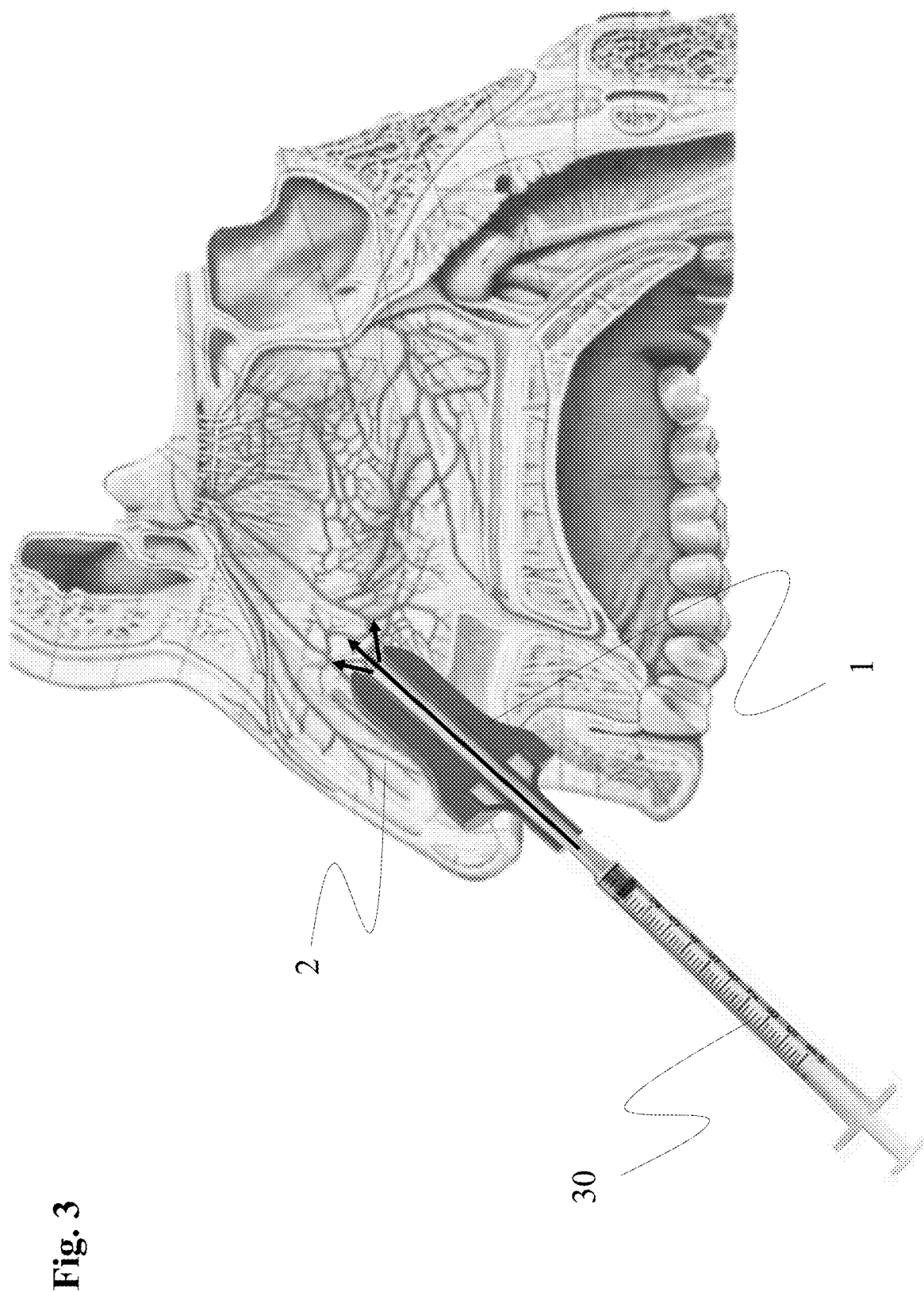
FIG. 3 is a cross-sectional view of the nasal cavity of a subject illustrating nasal administration of a substance using a plug with a syringe according to one embodiment of the present disclosure.

Referring now to FIG. 3, there is shown a syringe 30 to be used in conjunction with the plug 1 for delivery of fluid therapeutic agents to the nasal cavity of a subject according to one embodiment of the present disclosure, i.e. nasal administration. Here, the plug 1 acts as an adapter for injecting substances into the nose, either for topical administration of locally acting drugs, e.g. decongestants for cold and allergy treatment, or for systemic administration of systemically acting drugs, e.g. analgesics, nicotine or vaccines. A third route of administration achieved by the plug of the present disclosure is through olfactory transfer via the receptor nerve cells of the olfactory epithelium which project into the olfactory bulb of the brain. This provides a direct connection for delivery of drugs to the brain, bypassing the blood-brain barrier. This may be used to deliver drugs such as cerebral cytostatic for cancer, medicines for Alzheimer's disease and other neurodegenerative diseases, or inhibiting agents for cerebral AIDS or malaria by means of the plug 1.

In a first step, the plug 1 is compressed and inserted into the nostril 2 and allowed to expand such that it seals against the walls of the nostril 2. Next, the syringe 30 is inserted into the proximal opening 22 of the hollow tubular member 20 and the fluid therapeutic agent is injected through the plug 1 into the nasal cavity by depressing the plunger of the syringe 30. The plug 1 and the syringe 30 may be provided together in a pre-packaged kit for this purpose. Preferably, the syringe 30 is pre-filled with a fluid therapeutic agent to be delivered to the subject through the plug 1.

The therapeutic agent may be a pharmaceutical drug intended for parenteral or topical administration. Examples of suitable therapeutic agents include analgesics such as paracetamol/acetaminophen, nonsteroidal anti-inflammatory drugs (NSAIDs), opioids; corticosteroids such as cortisol, corticosterone, cortisone, aldosterone; antibiotics such as penicillins, cephalosporins, polymoxins, rifamycins, lipiarmycins, quinolones, sulfonamides, macrolides, lincosamides, tetracyclines, cyclic lipopeptides, glycylcyclines, oxazolidinones, lipiarmycins; decongestants such as pseudoephedrine, phenylephrine, antihistamines, naphazoline, oxymetazoline; stem cells; nicotine; vaccines; anti-viral agents; polysaccharide-glycan-based-substances, antioxidants; cerebral cytostatic; medicines for Alzheimer's disease and other neurodegenerative diseases; inhibiting agents for cerebral AIDS or malaria; disinfectants; astringents such as aluminum acetotartrate (ALSOL) solution, Burow's solution; procoagulants such as aluminum sulfate solution; antifungals such as clotrimazole and/or cerumenolytics such as olive oil, hydrogen peroxide.

Non-prescription drugs and therapeutic agents sold over-the-counter may be delivered and administered by the subject without the need for professional health care workers. More potent prescription drugs may require assistance from professional health care workers for delivery administration according to local health care regulations, to ensure correct dosage.

In a further embodiment of the present disclosure, the plug 1 is not limited to use in the nostril of a subject but may also be used to treat disorders of the ear. The human ear canal is of comparable dimension to the nostril and the plug 1 can, without any adjustments, be inserted into the ear and used in a similar procedure as described above in conjunction with FIG. 3.

Figure 4:
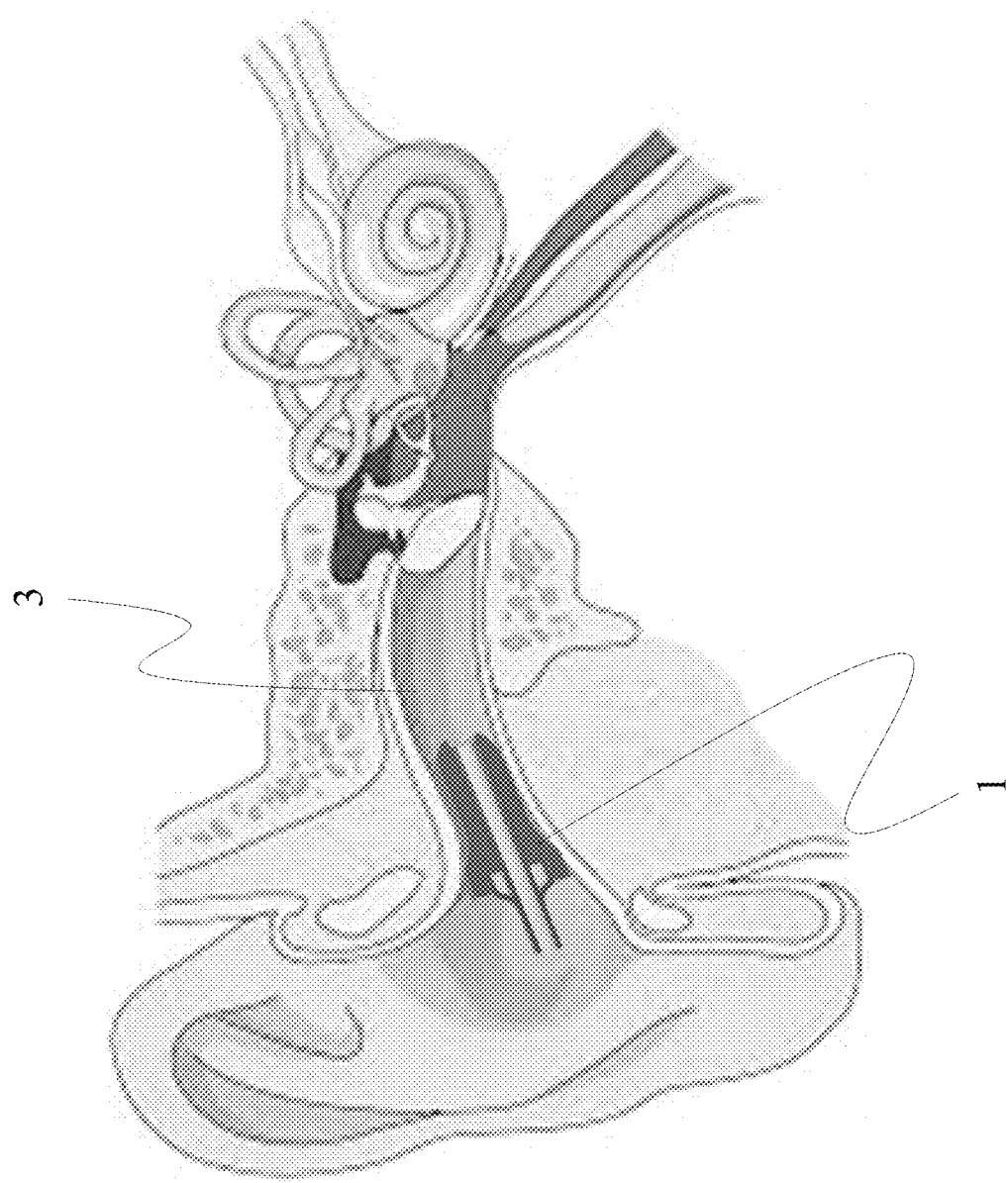
FIG. 4 is a cross-sectional view of the ear of a subject with a plug according to one embodiment of the present disclosure inserted into the ear canal.

Referring now to FIG. 4, there is shown a cross-sectional view of the ear of a subject, including a plug 1 inserted into the ear canal 3. In one embodiment, the plug is used in treatment of otitis externa, also known as swimmer's ear, which is an inflammation of the ear canal. To this end, the plug 1 can be soaked with disinfectant, decongestant and/or astringent substances like aluminum acetotartrate (ALSOL) solution or liquor for topical administration in the ear canal. Treatment of swimmer's ear often requires soaking of the ear canal several times per day. The plug 1 may remain inserted in the ear canal, and a syringe 30 may be used to deliver additional ALSOL solution as needed. The hollow tubular member 20 allows the subject to still hear while the plug 1 and collar 25 prevent the ALSOL solution from dripping out of the ear. Traditional treatment of today all block the ear canal and impair the hearing for the subject.

In one embodiment, the plug 1 may be used in treatment of cerumen impaction, i.e. excess earwax which blocks the ear canal. To this end, the plug 1 is inserted into the ear canal 3 and a cerumenolytic substance is injected through the tubular member 20 by means of a syringe 30. After injection, the proximal end 24 of the hollow tubular member 20 is closed, e.g. with a small rubber or plastic stopper (not shown), and the plug 1 is left in the ear canal 3 for an extended time period, e.g. overnight, allowing the cerumenolytic substance to soften and loosen the earwax to facilitate removal. The cerumenolytic substance may for instance be selected from mineral or vegetable oils (e.g. olive oil, almond oil, baby oil), glycerin, docusate, triethanolamine polypeptide. After sufficient time has passed, the stopper is removed and the remaining cerumenolytic substance and softened earwax is aspirated using a syringe 30 whilst simultaneously slowly removing the plug 1. This technique is a much gentler way of removing cerumen, especially for children and elderly, compared to conventional carbamide peroxide irrigation which can cause trauma to the ear canal and ear drum, vertigo, and pain or even inflammation.

Figure 5:
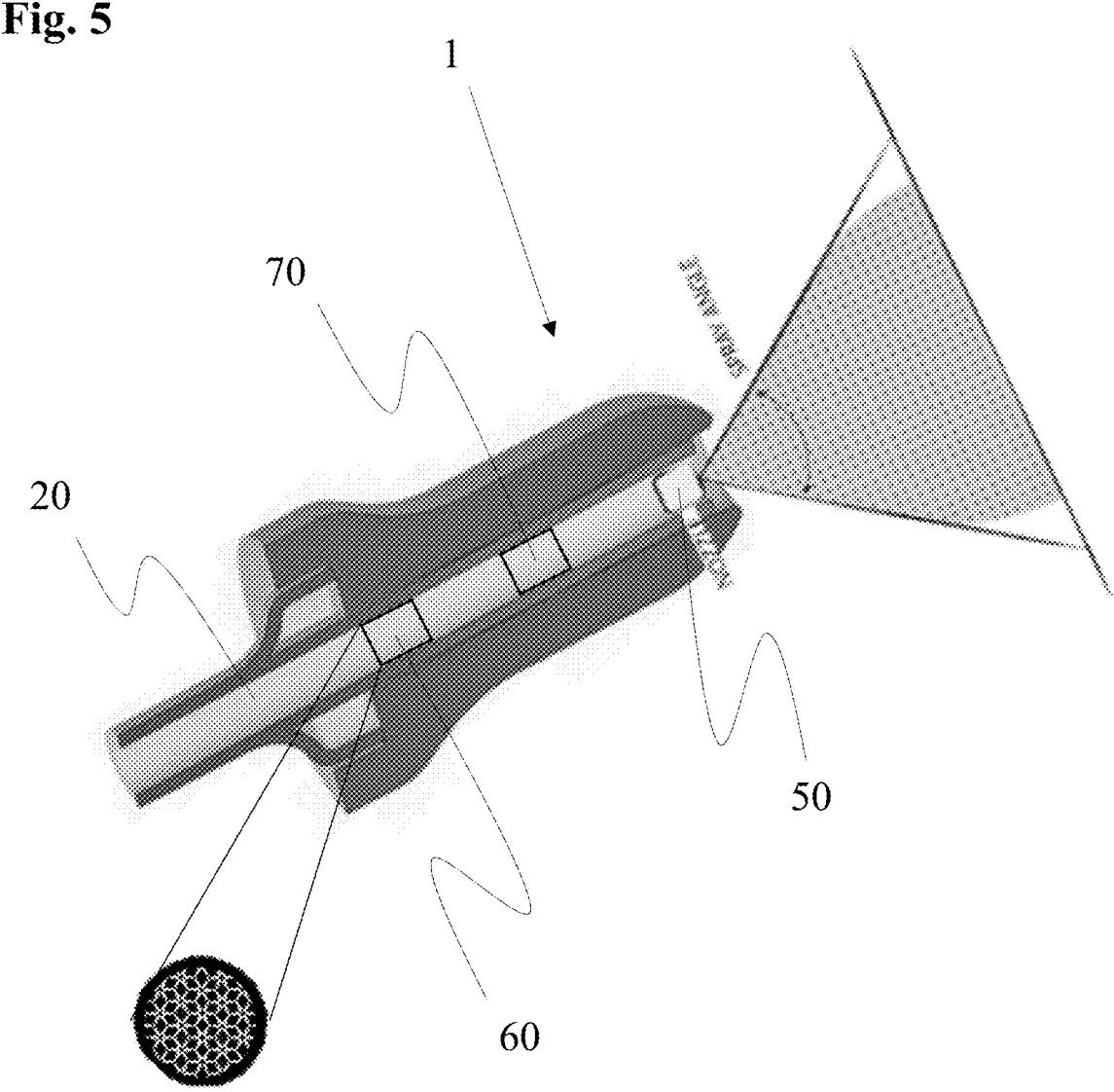
FIG. 5 is a cross-sectional view of a plug with additional components arranged inside the tubular member according to one embodiment of the present disclosure.

Referring now to FIG. 5, there is shown another embodiment of the plug 1 according to the present disclosure. In this embodiment, the plug 1 comprises one or more additional components arranged inside the hollow tubular member 20. Adjacent the first, distal end 21 of the hollow tubular member 20, there is arranged a spray nozzle 50. The spray nozzle 50 may in its simplest form be a single-fluid plain-orifice nozzle, but other configurations such as shaped-orifice nozzles and surface-impingement nozzles are also foreseen depending on the spray characteristics desired, as known in the art. Common for all types of single-fluid spray nozzles is that the fluid is passed through a small orifice which causes the fluid to break up into droplets, i.e. atomization, which are then distributed over a surface area, the nasal cavity in the case of nasal administration and the ear canal in the case of administration into the ear. The spray nozzle 50 is preferably configured to produce a cone-shaped spray with a spray angle as shown in FIG. 5. The spray nozzle 50 is further arranged proximal to the first, distal end 21 of the tubular member 20 such that the spray nozzle 50 does not rub against the nasal mucosa or epithelium of the ear canal 3.

Additionally or alternatively, a filter 60 is arranged inside the hollow tubular member 20. The filter 60 exhibits a plurality of openings or pores with a pore size adapted to prevent inhaled, intruding, infiltrated or penetrating particles such as dust, dirt, smoke, pollen, carcinogens, radioactive substances, and other irritants and/or microbes such as bacteria, parasites, amoebae, fungi, viruses (e.g. causing flu, common cold, and other airborne pandemic respiratory diseases, MERS, SARS-CoV, SARS-CoV-2 etc) from passing through the filter 60. In that way the nose or ear is protected from exposure to e.g. pathogens whilst allowing air to pass through the plug 1 to enable breathing or hearing, as opposed to known plugs which completely block the nostril 2 or ear canal 3.

Additionally or alternatively, an internal device 70 is arranged inside the hollow tubular member 20. The internal device 70 can be controlled via an app and can, for example, be used as an alarm clock or in virtual reality situations and emit designated scents/fragrances, vibrations, acoustic signals etc. as feedback or to notify the wearer of different situations that might arise and require his/her attention or action.

The internal device 70 may be a sensor for detecting gas (suffocating e.g. nitrogen, carbon dioxide, argon, flammable e.g. gasoline, hydrogen, methane, propane, toxic e.g. hydrogen sulfide, carbon monoxide, nitric oxide) or radioactivity, detect levels of pollen, pollution or pathogens and respond to that stimuli in different ways, and to emit pheromones, aphrodisiac, scents/fragrances and enhance smell. Many agents cannot be smelled by humans and that can be life threatening in different environments, and with a small sensor in the nose plug one can immediate get notifications (emitting different stimuli) about it. Also, many people suffer from more or less total loss of smell (anosmia) and a sensor placed in the plug has the advantage of being very close to the olfactory area (area for receptors for smell) up in the nose, and can enhance the smell and increase the quality of life.

In another embodiment, the internal device 70 may be an acoustic device such as a hearing aid, a speaker or an auditory masking device. The acoustic device provides the possibility to combine the plug with a wide range of technical applications such as audio communication, listening to music, detect auditory vibrations, acoustic trauma or inhibiting tinnitus by producing sound or noise.

In one embodiment, the internal device 70 is configured to determine a position and/or orientation of the plug 1. Examples of suitable internal devices include positioning or tracking devices such as markers or beacons emitting and/or receiving electromagnetic signals which may be used to determine the position. For instance, the tracking device may be used to determine position in conjunction with global navigation satellite systems such as GPS or local positioning systems using cellular base stations, Wi-Fi access points, and radio broadcast towers. Other examples of suitable devices include gyroscopes and accelerometers.

It is understood that although FIG. 5 illustrates the plug 1 with the spray nozzle 50, the filter 60 and the internal device 70 in combination, the plug 1 may comprise one or two or more of the additional components in different combinations, depending on the desired configuration, medical indication and use of the plug 1.

Although the description above contains a plurality of specificities, these should not be construed as limiting the scope of the concept described herein but as merely providing illustrations of some exemplifying embodiments of the described concept. It will be appreciated that the scope of the presently described concept fully encompasses other embodiments which may become obvious to those skilled in the art, and that the scope of the presently described concept is accordingly not to be limited. Reference to an element in the singular is not intended to mean "one and only one" unless explicitly so stated, but rather "one or more". Moreover, it is not necessary for an apparatus or method to address each and every problem sought to be solved by the presently described concept, for it to be encompassed hereby.

The invention claimed is:

1. A plug for insertion into a nose or ear of a subject, comprising:
   a body adapted to fit into a nostril or ear canal of the subject, the body comprising a first end arranged to face inward and a second end arranged to face outward during use, wherein the body comprises a compressible, resilient foam material adapted to absorb liquid;
   a hollow tubular member disposed inside the body and extending substantially an entire length of the body and comprising a tubular portion having a first opening facing inwardly and a second opening facing outward during use, the hollow tubular member being arranged to provide fluid communication between the first and second openings;
   wherein the hollow tubular member further comprises a cup-shaped collar arranged on an external surface of the tubular portion and extending radially outward from the tubular portion, wherein a rim of the collar, defined by a radially outermost surface of the collar, is disposed inside the body in contact with an inner wall of the body at the second end of the body, wherein a substantially concave side of the collar faces towards the first end of the body; and
   wherein the second opening of the hollow tubular member is adapted to receive a tip of a syringe for injection of a fluid therapeutic agent through the hollow tubular member.

2. The plug according to claim 1, further comprising a spray nozzle arranged adjacent the first opening of the hollow tubular member.

3. The plug according to claim 1, further comprising a filter arranged inside the hollow tubular member.

4. The plug according to claim 1, further comprising an internal device arranged inside the hollow tubular member.

5. The plug according to claim 4, wherein the internal device is an acoustic device being selected from a hearing aid, a speaker or an auditory masking device.

6. The plug according to claim 4, wherein the internal device is a sensor, the sensor being configured to detect gas, radioactivity, levels of pollen, pollution, pathogens, acoustic signals and/or electromagnetic signals.

7. The plug according to claim 6, wherein the sensor is configured to emit pheromones, aphrodisiac, scents/fragrances, vibrations and/or acoustic signals in response to the detection.

8. The plug according to claim 4, wherein the internal device is configured to determine a position and/or orientation of the plug.

9. A kit comprising at least one plug for insertion into the nose or ear of a subject and at least one syringe pre-filled with a fluid to be injected into the nostril or ear canal of the subject through the plug, the plug comprising:
   a body adapted to fit into a nostril or ear canal of the subject, the body comprising a first end arranged to face inward and a second end arranged to face outward during use, wherein the body comprises a compressible, resilient foam material adapted to absorb liquid;
   a hollow tubular member disposed inside the body and extending substantially an entire length of the body and comprising a tubular portion having a first opening facing inwardly and a second opening facing outward during use, the hollow tubular member being arranged to provide fluid communication between the first and second openings;
   wherein the hollow tubular member further comprises a cup-shaped collar arranged on an external surface of the tubular portion and extending radially outward from the tubular portion, wherein a rim of the collar, defined by a radially outermost surface of the collar, is disposed inside the body in contact with an inner wall of the body at the second end of the body, wherein a substantially concave side of the collar faces towards the first end of the body; and
   wherein the second opening of the hollow tubular member is adapted to receive a tip of the syringe for injection of a fluid therapeutic agent through the hollow tubular member.

10. The kit according to claim 9 further comprising a spray nozzle arranged adjacent the first opening of the hollow tubular member.

11. The kit according to claim 9, further comprising a filter arranged inside the hollow tubular member.

12. The kit according to claim 9, further comprising an internal device arranged inside the hollow tubular member.

13. The kit according to claim 12, wherein the internal device is an acoustic device being selected from a hearing aid, a speaker or an auditory masking device.

14. The kit according to claim 12, wherein the internal device is a sensor, the sensor being configured to detect gas, radioactivity, levels of pollen, pollution, pathogens, acoustic signals and/or electromagnetic signals.

15. The kit according to claim 14, wherein the sensor is configured to emit pheromones, aphrodisiac, scents/fragrances, vibrations and/or acoustic signals in response to the detection.

16. The kit according to claim 12, wherein the internal device is configured to determine a position and/or orientation of the plug.

17. The kit according to claim 9, wherein the fluid therapeutic agent is selected from analgesics, corticosteroids, antibiotics, decongestants, stem cells, nicotine, vaccines, cerebral cytostatic, disinfectants, astringents, procoagulants, antifungals and/or cerumenolytics.

* * * * *